United States Patent
Sheridan

(10) Patent No.: US 8,415,121 B2
(45) Date of Patent: Apr. 9, 2013

(54) PROCESS FOR THE MANUFACTURE OF LAIDLOMYCIN

(75) Inventor: Robert Sheridan, Marietta, OH (US)

(73) Assignee: Alpharma, LLC, Bridgewater, NJ (US)

( * ) Notice: Subject to any disclaimer, the term of this patent is extended or adjusted under 35 U.S.C. 154(b) by 79 days.

(21) Appl. No.: 12/887,807

(22) Filed: Sep. 22, 2010

(65) Prior Publication Data
US 2011/0082303 A1 Apr. 7, 2011

Related U.S. Application Data

(60) Provisional application No. 61/278,280, filed on Oct. 5, 2009.

(51) Int. Cl.
*C12P 19/52* (2006.01)
*C12P 17/16* (2006.01)
*C12P 17/18* (2006.01)
*C07D 407/00* (2006.01)

(52) U.S. Cl.
USPC .............. 435/83; 435/118; 435/119; 549/414

(58) Field of Classification Search ..................... None
See application file for complete search history.

(56) References Cited

U.S. PATENT DOCUMENTS

| | | |
|---|---|---|
| 4,394,377 A | 7/1983 | Spires |
| 4,405,609 A | 9/1983 | Potter |
| 4,431,665 A | 2/1984 | Kluge et al. |
| 4,478,935 A | 10/1984 | Williams et al. |
| 4,542,027 A | 9/1985 | Clark |
| 4,582,853 A | 4/1986 | Liu et al. |
| 4,824,863 A | 4/1989 | Hamill et al. |
| 4,933,364 A | 6/1990 | Ivy et al. |
| 5,041,374 A * | 8/1991 | Chu et al. ...................... 435/118 |
| 5,047,338 A | 9/1991 | Miescher et al. |
| 5,049,495 A | 9/1991 | Miescher et al. |
| 5,152,995 A | 10/1992 | Runkel et al. |
| 5,273,752 A | 12/1993 | Ayer et al. |
| 5,462,741 A | 10/1995 | Carr et al. |
| 5,541,224 A | 7/1996 | O'Doherty |
| 5,874,103 A | 2/1999 | Moore et al. |
| 6,365,174 B1 | 4/2002 | Lowe et al. |
| 6,441,208 B2 | 8/2002 | Bijl et al. |
| 6,458,377 B1 | 10/2002 | Lowe et al. |
| 6,727,373 B2 | 4/2004 | Bijl et al. |
| 7,416,742 B2 | 8/2008 | McNeff et al. |
| 2001/0025114 A1 | 9/2001 | Bijl et al. |
| 2003/0143659 A1 | 7/2003 | Bijl et al. |
| 2003/0152689 A1 | 8/2003 | Ethington et al. |
| 2004/0071782 A1 | 4/2004 | Agnew et al. |
| 2004/0247568 A1 | 12/2004 | Guerino et al. |
| 2006/0003022 A1 | 1/2006 | McNeff et al. |
| 2007/0116729 A1 | 5/2007 | Palepu |
| 2008/0274211 A1 | 11/2008 | McNeff et al. |

OTHER PUBLICATIONS

RK McGuffey et al., Ionophores for Dairy Cattle: Current Status and Future Outlook, J. Dairy Sci. 84 (E Supp.) E194-203, (2001).

* cited by examiner

*Primary Examiner* — Rebecca Prouty
*Assistant Examiner* — Paul Martin
(74) *Attorney, Agent, or Firm* — Martha A. Gammill

(57) ABSTRACT

Improved process for the isolation of laidlomycin from a fermentation broth includes increasing the pH of the fermentation broth and centrifuging the pH adjusted fermentation broth, resulting in an aqueous layer and a wet solid layer containing laidlomycin. After the aqueous layer is removed, the wet solid layer containing laidlomycin is dried. The process provides an efficient and high yielding method.

5 Claims, No Drawings

PROCESS FOR THE MANUFACTURE OF LAIDLOMYCIN

CROSS REFERENCE TO RELATED APPLICATIONS

This application claims priority to U.S. Ser. No. 61/278,280 filed Oct. 5, 2009 which is incorporated in its entirety by reference herein.

BACKGROUND

Laidlomycin is a polyether antibiotic that has been shown to inhibit the growth of Gram positive and ruminant bacteria. Laidlomycin has also been shown to increase the efficiency of feed utilization and rate of weight gain in domestic animals, especially meat-producing and milk-producing animals, such as cattle. Carbohydrates form a large part of these animals' diets, and the efficiency of carbohydrate utilization is desirably increased by treatment which encourages intraruminal production of propionate rather than acetate from carbohydrates. Additionally, laidlomycin suppresses rumen lactic acid production, thereby assisting in the prevention or treatment of bloat in ruminant animals.

Typically, laidlomycin is prepared by fermentation of organisms such as Streptoverticillium eurocidicum in a nutrient-containing aqueous broth containing sources of assimilable carbon and nitrogen. Known isolation processes to recover polyether antibiotics from the fermentation broth include complex, multistage solvent extraction processes. Other processes include the addition of hydrophobic materials such as glycerides and fatty acids to adsorb on the polyether antibiotic to form agglomerates. Such hydrophobic materials, however, need to be removed from the polyether antibiotic in a purification step.

There remains a need for alternative processes to isolate laidlomycin.

BRIEF SUMMARY

In one embodiment of the present invention, a method of isolating laidlomycin from a fermentation broth comprises adjusting the pH of an aqueous fermentation broth comprising laidlomycin to about 10 to about 13; allowing the pH adjusted aqueous fermentation broth to form an emulsion; centrifuging the emulsion to form an aqueous layer and a wet solid layer containing laidlomycin; and drying the wet solid layer containing laidlomycin to form a dry solid containing laidlomycin.

The above-described and other features will be appreciated and understood by those skilled in the art from the following detailed description and appended claims.

DETAILED DESCRIPTION

Disclosed herein is a convenient and efficient process of isolating laidlomycin from a fermentation broth by increasing the pH of the fermentation broth to form an emulsion. The emulsion is then centrifuged to form an aqueous layer and a wet solid layer. The wet solid contains laidlomycin and the biomass from the fermentation process. The wet solid may be washed with water to remove soluble fermentation material. The wet solid is then dried to remove any water. The resulting dry solid contains about 15% to about 80% laidlomycin, preferably from about 20% to about 60% laidlomycin. The resulting dry solid may be further washed with a non-polar hydrocarbon solvent, such as hexane, to remove any excess oil or impurities. The process is an improvement over known processes as no additional hydrophobic materials such as glycerides, fatty acids, or combinations thereof are added to the broth at the end of fermentation and thus steps to remove additional hydrophobic material is not necessary. Furthermore, the isolation process results in a reduced quantity of material that may be the subject of further processing including purification, while at the same time providing a good material recovery of the laidlomycin product. Smaller volumes of material to be purified require smaller amounts of solvents.

Laidlomycin is prepared by fermentation of organisms such as Streptoverticillium eurocidicum in a nutrient-containing aqueous broth containing water, sources of assimilable carbon and nitrogen, and other fermentation ingredients known in the art. The assimilable carbon sources include fats and oils, free fatty acids, phospholipids (e.g., lecithin), and combinations thereof. Exemplary assimilable carbon sources include glycerides such as soybean oil, safflower oil, cottonseed oil, sesame oil, olive oil, rape oil, peanut oil, corn oil, sunflower oil and the like, or animal/fish fat and oil; fatty acids such as lauric acid, myristic acid, palmitic acid, stearic acid, arachidic acid, lignoceric acid, palmitoleic acid, oleic acid, linoleic acid, linolenic acid, arachidonic acid and the like; and combinations thereof.

Exemplary assimilable sources of nitrogen include yeast, yeast-derivate products, enzyme-hydrolyzed caseine, peptones, cornmeal, soybean meal, cottonseed meal, amino acids, and combinations thereof. Other fermentation ingredients may include inorganic soluble salts such as those having a cation of sodium, magnesium, calcium, and ammonium with a corresponding anion of chloride, carbonate, sulfate, nitrate, and the like. Other additives useful for the growth and development of the Streptoverticillium eurocidicum microorganism as known in the art can also be included in the culture.

The fermentation process can generally be carried out at temperatures slightly above ambient for several days. The pH of a fermentation broth during main fermentation can be about 5.5 to about 8.0, specifically about 6.0 to about 7.5, and more specifically about 6.5 to about 7.0.

The fermentation broth at the end of fermentation typically contains laidlomycin A, laidlomycin B, derivatives of laidlomycin (e.g., 26-desoxylaidlomycin), remaining unused assimilable carbon or nitrogen sources, salts, water, and fermentation additives.

To provide efficient and rapid separation of the aqueous and lipid phases of the fermentation broth at the end of fermentation, the pH is increased to about 10 to about 13, preferably from about 10.5 to about 11 to produce an emulsion. The resulting emulsion is centrifuged, forming an aqueous layer and a wet solid layer. The aqueous layer is decanted off, and the wet solid layer is washed one or more times with water. With each wash, water is added to and mixed with the wet solid layer, the mixture is centrifuged, and the resulting aqueous layer is decanted off. After the final aqueous layer is removed, the wet solid layer is dried in a dryer. The wet solid may be washed with a non-polar hydrocarbon solvent, such as hexane, prior to drying in the dryer or after drying in the dryer to remove any excess oils.

In one embodiment, no lipophilic or hydrophobic solvents or additives are added to the fermentation broth prior to isolating the laidlomycin, and no extraction with solvents is performed prior to isolating the laidlomycin.

The pH of the aqueous fermentation broth may be increased by the addition of a mineral base. The mineral base may be used in concentrated form or diluted with water. Exemplary mineral bases include but are not limited to sodium hydroxide and potassium hydroxide. In a specific embodiment, the mineral base is sodium hydroxide.

The wet solid phase from the disclosed processes can be further processed or purified to remove by-products from fermentation including remaining assimilable carbon and nitrogen sources, impurities, and the like. The processing can include techniques known in the art including extraction, precipitation, salt formation, crystallization, column chromatography, or a combination thereof. Laidlomycin sodium may be extracted from the wet solid phase with an organic solvent, including but not limited to methylene chloride, ethyl acetate, and methyl isobutyl ketone.

The laidlomycin sodium salt recovered from the wet solid phase may undergo propanoylation to form the laidlomycin propionate potassium salt (LPK). Laidlomycin sodium salt, methylene chloride, and 4-dimethylaminopyridine are combined and refluxed. Water is removed by azeotropic distillation, and the resulting material is transferred to a vessel and cooled to around 20° C.±5° C. under a nitrogen atmosphere. Propionic anhydride is added to the vessel and the temperature is adjusted to around 20° C.±5° C. and held at this temperature until the reaction is complete. When the level of laidlomycin is not more than 2.2% laidlomycin (LDL), the reaction solution is quenched with an aqueous potassium bicarbonate solution. Once the reaction has been quenched, the reaction solution is held to ensure completion of the reaction. If the level of mixed anhydrides is not more than 2%, then the organic layer is separated from the aqueous layer. The aqueous phase is extracted with methylene chloride and the methylene chloride layers are combined. The aqueous phase is discarded. The combined methylene chloride layers are extracted with water, or with an approximately 20% potassium chloride solution. The organic layer is separated and the aqueous phase is extracted with methylene chloride, and the methylene chloride layers are combined. The aqueous phase is discarded. This aqueous extraction sequence of the methylene chloride layer may be repeated. The methylene chloride/product layer is then dried by azeotropic distillation. Vacuum is then applied to remove most of the methylene chloride. The residual methylene chloride is removed by adding methanol and distilling the solution under vacuum. This step is then repeated. The batch is then cooled to around 15-20° C. Water is added in an amount ranging from about 76-100% w/w to precipitate the free fatty acids from the LDL fermentation process. The solution is then filtered through diatomaceous earth, and the filter is rinsed with a mixture of methanol and water. A solution of potassium bicarbonate is slowly added to the solution to precipitate the LPK. The batch is allowed to age for about one hour before centrifuging. The product is dried under vacuum with a jacket temperature of approximately 65-70° C.

The invention is further illustrated by the following non-limiting examples.

EXAMPLES

Example 1

Isolation of laidlomycin from fermentation broth. A stock broth of laidlomycin (LDL) from the fermentation of *Streptoverticillium eurocidicum* was adjusted to a pH greater than 10.5 with sodium hydroxide. The free fatty acid (FFA) concentration of the broth was 2.80%. The addition of the sodium hydroxide caused the broth to form an emulsion. After the pH adjustment, approximately 350 grams of the emulsion were poured into six (6) centrifuge tubes. The centrifuge tubes were spun at 6000 rpm for 15 minutes, resulting in the separation of the emulsion into a liquid layer and a wet solid layer in each of the tubes. The liquid layers were decanted off, leaving a layer of wet solid biomass in each tube.

Approximately 100 mls of water were added to each tube containing the wet solid biomass. The tubes were mixed vigorously and a Teflon stir bar was added to help with the mixing of the water and the biomass. The tubes were centrifuged at 6000 rpm for 15 minutes. The resulting liquid layer was decanted off, and the resulting biomass layer was washed again with about 100 mls of water and centrifuged at 6000 rpm for 15 minutes. The resulting liquid layer was decanted off, and the resulting biomass layer was washed for a third time with about 100 mls of water. The tubes were centrifuged at 6000 rpm for 15 minutes, and the resulting liquid layer was decanted off. The resulting biomass layer was weighed.

The biomass from each tube was placed in a 55° C. oven overnight for 15 hours. The biomass was then placed on a freeze dryer at ambient temperature overnight for 18 hours, and then finally placed into a vacuum oven for 3 hours. The amount of LDL in each phase was determined by HPLC analysis. The results of this experiment are provided in Table 1 below where the g/kg values are expressed in terms of kilograms of sample.

TABLE 1

| Sample | LDL A g/kg | LDL B g/kg | Total LDL g/kg | Sample Weight (g) | Contained LDL (g) | % of contained LDL | Normalized % LDL |
|---|---|---|---|---|---|---|---|
| Starting broth | 11.16 | 1.47 | 12.63 | 2089.77 | 26.39 | | |
| Initial decant | 0.98 | 0.14 | 1.12 | 1537.41 | 1.72 | 6.52 | 6.65 |
| Wash 1 | 0.51 | 0.07 | 0.58 | 642.57 | 0.37 | 1.41 | 1.44 |
| Wash 2 | 0.29 | 0.03 | 0.32 | 579.10 | 0.19 | 0.70 | 0.72 |
| Wash 3 | 0.20 | 0.02 | 0.22 | 752.12 | 0.17 | 0.63 | 0.64 |
| Dry Solids | 199.65 | 27.81 | 227.46 | 103.14 | 23.46 | 88.89 | 90.56 |
| Total LDL | | | | | 25.91 | | |
| % LDL recovered | | | | | 98.15 | | 100.00 |

Example 2

Isolation of laidlomycin from fermentation broth having higher oil content. Another stock broth of laidlomycin (LDL) from the fermentation of *Streptoverticillium eurocidicum* having a different FFA and oil composition was adjusted to a pH of greater than 10.5 with sodium hydroxide. The FFA concentration was 2.98%. The addition of the sodium hydroxide caused the broth to form an emulsion. After the pH adjustment, approximately 300 grams of the emulsion were poured into five (5) centrifuge tubes. The centrifuge tubes were spun at 7000 rpm for 10 minutes, resulting in the separation of the emulsion into a liquid layer and a wet solid layer in each of the tubes. The liquid layers were decanted off, leaving a layer of wet solid biomass in each tube.

Approximately 100 mls of water were added to each tube containing the wet solid biomass. The tubes were mixed vigorously and a Teflon stir bar was added to help with the mixing of the water and the biomass. The tubes were centrifuged at 7000 rpm for 10 minutes. The resulting liquid layer was decanted off, and the resulting biomass layer was washed again with about 100 mls of water and centrifuged at 7000 rpm for 10 minutes. The resulting liquid layer was decanted off, and the resulting biomass layer was washed for a third time with about 100 mls of water. The tubes were centrifuged at 7000 rpm for 10 minutes, and the resulting liquid layer was decanted off. The resulting biomass layer was weighed.

The biomass from each tube was placed in a 55° C. oven overnight for 15 hours. The biomass was then placed on a freeze dryer at ambient temperature overnight for 18 hours, and then finally placed into a vacuum oven for 3 hours. The amount of LDL in each phase was determined by HPLC analysis. The results of this experiment are provided in Table 2 below where the g/kg values are expressed in terms of kilograms of sample.

TABLE 2

| Sample | LDL A g/kg | LDL B g/kg | Total LDL g/kg | Sample Weight (g) | Contained LDL (g) | % of cont'd LDL | Normalized % LDL |
|---|---|---|---|---|---|---|---|
| Starting broth | 12.88 | 1.68 | 14.56 | 1489.93 | 21.69 | | |
| Initial decant | 2.01 | 0.25 | 2.26 | 860.61 | 1.94 | 8.97 | 8.63 |
| Wash 1 | 1.32 | 0.17 | 1.49 | 631.42 | 0.94 | 4.34 | 4.17 |
| Wash 2 | 0.71 | 0.09 | 0.80 | 512.31 | 0.41 | 1.89 | 1.82 |
| Wash 3 | 0.27 | 0.04 | 0.31 | 524.76 | 0.16 | 0.75 | 0.72 |
| Dry Solids | 178.19 | 23.68 | 201.87 | 94.57 | 19.09 | 88.00 | 84.66 |
| Total LDL | | | | | 22.55 | | |
| % LDL recovered | | | | | 103.94 | | 100.00 |

As shown in Table 2, the higher oil content broth gives about a 5% less LDL recovery.

Example 3

Isolation of laidlomycin from fermentation broths having different pHs. A stock broth of laidlomycin (LDL) from the fermentation of *Streptoverticillium eurocidicum*, having a pH of 3.58, was divided into three (3) samples, labeled A, B, and C. The pH of Sample A was left at 3.58. The pH of Sample B was adjusted to 10.9 with 50% sodium hydroxide. Six centrifuge tubes containing about 350 gms of Sample A each and six centrifuge tubes containing about 350 gms of Sample B each were processed according to the protocol of Example 2.

The pH of Sample C was adjusted to 11.13 with 50% sodium hydroxide. Six centrifuge tubes contain about 350 gms of Sample C each were processed according to the protocol of Example 2, with the exception of the third wash. After the second wash, 100 ml of water was added to each tube. The contents of each tube were poured into a 1500 ml beaker. A mechanical stirrer was added to the beaker and the pH was adjusted to 4.89 with concentrated sulfuric acid. The contents of the beaker were divided into four, 500 ml centrifuge tubes. The tubes were centrifuged at 7000 rpm for 10 minutes. The liquid layer was poured off and the resulting wet solids were placed in a 55° C. oven overnight for 15 hours, and then placed in a freeze dryer at ambient temperature for 18 hours. The results are shown in Table 3 where the g/kg values are expressed in terms of kilograms of sample.

TABLE 3

| Sample | LDL A g/kg | LDL B g/kg | Total LDL g/kg | Sample Weight (g) | Contained LDL (g) | % of cont'd LDL | Normalized % LDL |
|---|---|---|---|---|---|---|---|
| Sample A | | | | | | | |
| Starting broth | 8.41 | 1.33 | 9.74 | 2086.19 | 20.32 | | |
| Initial decant | 1.17 | 0.23 | 1.40 | 1688.62 | 2.36 | 11.63 | 11.90 |
| Wash 1 | 0.57 | 0.09 | 0.66 | 602.38 | 0.40 | 1.96 | 2.00 |
| Wash 2 | 0.46 | 0.08 | 0.54 | 616.33 | 0.33 | 1.64 | 1.68 |
| Wash 3 | 0.25 | 0.04 | 0.29 | 637.76 | 0.18 | 0.91 | 0.93 |
| Dry Solids | 126.10 | 19.90 | 146.00 | 113.62 | 16.59 | 81.64 | 83.49 |
| Total LDL | | | | | 19.87 | | |
| % LDL recovered | | | | | 97.78 | | 100.00 |
| Sample B | | | | | | | |
| Starting broth | 8.97 | 1.46 | 10.42 | 2087.56 | 21.75 | | |
| Initial decant | 2.03 | 0.38 | 2.41 | 1569.55 | 3.78 | 17.39 | 18.20 |
| Wash 1 | 1.00 | 0.17 | 1.17 | 661.33 | 0.77 | 3.56 | 3.72 |
| Wash 2 | 0.52 | 0.08 | 0.60 | 593.10 | 0.36 | 1.64 | 1.71 |
| Wash 3 | 0.34 | 0.05 | 0.39 | 632.38 | 0.25 | 1.13 | 1.19 |

TABLE 3-continued

| Sample | LDL A g/kg | LDL B g/kg | Total LDL g/kg | Sample Weight (g) | Contained LDL (g) | % of cont'd LDL | Normalized % LDL |
|---|---|---|---|---|---|---|---|
| Dry Solids | 154.27 | 23.49 | 177.76 | 87.92 | 15.63 | 71.85 | 75.18 |
| | | | Total LDL | | 20.79 | | |
| | | | % LDL recovered | | 95.56 | | 100.00 |
| Sample C | | | | | | | |
| Starting broth | 7.50 | 1.24 | 8.73 | 1786.61 | 15.60 | | |
| Initial decant | 3.20 | 0.52 | 3.72 | 1027.35 | 3.82 | 24.50 | 18.28 |
| Wash 1 | 1.85 | 0.30 | 2.15 | 834.76 | 1.79 | 11.51 | 8.58 |
| Wash 2 | 0.76 | 0.13 | 0.89 | 646.36 | 0.58 | 3.69 | 2.75 |
| Wash 3 | 0.43 | 0.07 | 0.50 | 1396.76 | 0.70 | 4.48 | 3.34 |
| Dry Solids | 173.05 | 28.57 | 201.62 | 69.52 | 14.02 | 89.87 | 67.04 |
| | | | Total LDL | | 20.91 | | |
| | | | % LDL recovered | | 134.04 | | 100.00 |

Example 4

Extraction and Propionation of Sample B. 81.67 grams of Sample B biomass (from Example 3) above was placed into a 500 ml Erlenmeyer flask. 100 ml of hexane was added to the 500 ml Erlenmeyer flask and swirled with the biomass for several minutes. The mixture was filtered through a Buchner funnel, and the solids were air dried. The dried solids were placed back into the 500 ml Erlenmeyer flask, washed with 100 ml of fresh hexane, and filtered again. The hexanes were transferred to a Rb flask, and the hexane was stripped off on a rotovap. 20.68 grams of oil/solids were collected.

The air-dried solids were placed back into the 500 ml Erlenmeyer flask. 100 mls of methylene chloride were added to the 500 ml Erlenmeyer flask, swirled, and allowed to stand for 10-15 minutes. The mixture was filtered through a Buchner funnel. The solids were extracted with methylene chloride two more times for a total of three (3) extractions. The methylene chloride was transferred to a 500 ml Rb flask and the methylene chloride was removed with a rotovap. 18.26 grams of an oily solid were collected.

18.26 grams of the oily solid were charged with 50 ml methylene chloride in a flask. 0.35 grams of 4-dimethylaminopyridien and 7.4 mls of propionic anhydride were added to the flask. The temperature was maintained at about 21 to about 26° C. with stirring for about eleven (11) hours. The mixture was then quenched with 11.20 grams of potassium bicarbonate in 55.06 grams of water. The resulting mixture was poured into a separator funnel, and the reaction flask was washed with about 50 mls of methylene chloride. The aqueous phase was extracted with about 25 mls of methylene chloride and the methylene chloride layers were combined. The aqueous phase was discarded. The combined methylene chloride layers were extracted with about 50 mls water. The organic layer was separated and the aqueous phase was extracted with about 25 mls methylene chloride, and the methylene chloride layers were combined. The aqueous phase was discarded. This aqueous extraction sequence of the methylene chloride layer may be repeated. The methylene chloride/product layer was then dried by azeotropic distillation. Vacuum was then applied to remove most of the methylene chloride. 20.40 grams of a brown solid were collected. The residual methylene chloride was removed by adding 70 mls methanol and the solution was distilled under vacuum. This step was then repeated. The batch was then cooled to around 15-20° C. 8 mls of a solution containing 5.10 grams potassium carbonate in 98.1 grams of water was slowly added to the solution. The resulting mixture was then filtered through a separator funnel, and the funnel was rinsed with a mixture of methanol and water. The batch was allowed to age for about one hour before centrifuging. The product was dried under vacuum with a jacket temperature of approximately 65-70° C. 13.63 grams of a white solid was recovered.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality. The terms "comprising", "having", "including", and "containing" are to be construed as open-ended terms (i.e., meaning "including, but not limited to") unless otherwise noted. The term "or" means and/or unless otherwise indicated. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

What is claimed is:

1. A method of isolating laidlomycin from a fermentation broth, comprising:
adjusting the pH of an aqueous fermentation broth comprising laidlomycin and a lipid material to about 10 to about 13 to form an emulsion;
centrifuging the emulsion to form an aqueous layer and a wet solid layer;
removing the aqueous layer; and
drying the wet solid layer thereby isolating the laidlomycin; wherein no lipophilic or hydrophobic solvents or additives are added to the fermentation broth prior to isolating the laidlomycin, and wherein no solvent extraction is performed prior to isolating the laidlomycin.

2. The method of claim 1, wherein the pH is adjusted to about 10.5 to about 11.

3. The method of claim 2, wherein the pH is adjusted to 10.5.

4. The method of claim 1, wherein a mineral base is used to adjust the pH.

5. The method of claim 4 wherein the mineral base sodium hydroxide is used to adjust the pH.

* * * * *